United States Patent [19]

Philipp et al.

[11] 4,431,657
[45] Feb. 14, 1984

[54] ANALGESIC COMPOSITIONS CONSISTING OF 2H-BENZOTHIENO[3,2-C]PYRAZOL-3-AMINE DERIVATIVES

[75] Inventors: Adolf Philipp, St. Laurent; Ivo Jirkovsky, Montreal; Rene Martel, Candiac, all of Canada

[73] Assignee: Ayerst, McKenna & Harrison Inc., Montreal, Canada

[21] Appl. No.: 380,974

[22] Filed: May 24, 1982

[51] Int. Cl.$^3$ .................. C07D 495/04; A61K 31/415
[52] U.S. Cl. ................................ 424/273 P; 548/359; 548/370
[58] Field of Search .............................. 548/359, 370; 424/273 P

[56] References Cited

U.S. PATENT DOCUMENTS 4,051,252  9/1977  Mayer et al. ......................... 548/359
4,140,785  2/1979  Hoffman et al. ................ 424/273 P

OTHER PUBLICATIONS

W. J. Barry et al., J. Chem. Soc., 4974 (1956).
S. B. Awad et al., Aust. J. Chem., 28, 601 (1975).
K. E. Chippendale et al., J. Chem. Soc., Perkin Trans. I, 129 (1973).
F. Sauter et al., Monatsh. Chem., 105, 869 (1974).

Primary Examiner—Henry R. Jiles
Assistant Examiner—K. Briscoe
Attorney, Agent, or Firm—Arthur E. Wilfond

[57] ABSTRACT

Herein is disclosed 2H-benzothieno[3,2-c]pyrazol-3-amine derivatives, therapeutically acceptable acid addition salts thereof, processes for their preparation, methods of using the derivatives and pharmaceutical compositions. The derivatives are useful for producing analgesia in a mammal. In addition, some of the derivatives are useful for inhibiting gastric acid secretion, convulsions, anxiety and aggression, and producing muscle relaxation, hypnosis and sedation in a mammal.

5 Claims, No Drawings

ANALGESIC COMPOSITIONS CONSISTING OF 2H-BENZOTHIENO[3,2-C]PYRAZOL-3-AMINE DERIVATIVES

RELATED APPLICATIONS

Related hereto are U.S. patent application Ser. No. (380,973) and U.S. patent application Ser. No. (380,972), both filed on the same date as this application.

BACKGROUND OF THE INVENTION

This invention relates to novel 2H-benzothieno[3,2-c]pyrazol-3-amine derivatives, to therapeutically acceptable acid addition salts thereof, to processes for their preparation, to methods of using the derivatives, and to pharmaceutical compositions of the derivatives. These derivatives are useful for producing analgesia in a mammal without objectionable side effects of the narcotic analgesic agents. Furthermore, the derivatives produce useful analgesia at doses, which do neither exhibit antiinflammatory nor paralytic effects. In addition, some of the derivatives are useful for inhibiting convulsions, anxiety and aggression, for producing muscle relaxation, and hypnosis, and for inhibiting gastric acid secretion in a mammal.

A number of benzothieno[3,2-c]pyrazole derivatives are known and described, for example, W. J. Barry et al., J. Chem. Soc., 4974 (1956); S. B. Awad et al., Aust. J. Chem., 28, 601 (1975); K. E. Chippendale et al., J. Chem. Soc., Perkin Trans. I, 129 (1973); and F. Sauter et al., Monatsh. Chem., 105, 869 (1974). The compounds reported in the above references lack the substituents on the benzothieno[3,2-c]pyrazole ring system which are characteristic of the compounds of this invention.

A number of 1H-benzothieno[3,2-c]pyrazol-3-amines are disclosed by H. E. Hoffmann et al., U.S. Pat. No. 4,140,785, issued Feb. 20, 1979. The latter amines are readily differentiated from the compounds of this invention by having a methyl or ethyl group at position 1 of the ring system and by having as their sole use chemical intermediates for preparing compounds useful in the treatment of diseases caused by rhinoviruses.

SUMMARY OF THE INVENTION

The compounds of this invention are represented by formula I

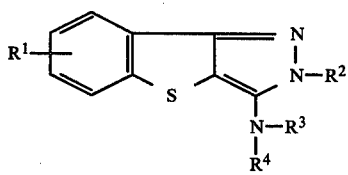

in which $R^1$ is hydrogen, halogen, lower alkyl, lower alkoxy or trifluoromethyl; $R^2$ is lower alkyl; $R^3$ is hydrogen, lower alkyl, trihalomethyl(lower)alkyl; oxo(lower)alkyl; or lower alkanoyl; and $R^4$ is hydrogen or lower alkyl; or a therapeutically acceptable acid addition salt thereof.

A preferred group of compounds of this invention is represented by formula I in which $R^1$ is hydrogen, bromo, chloro, or lower alkyl; $R^2$ is methyl; $R^3$ is hydrogen, lower alkyl, trifluoromethyl(lower)alkyl or oxo(lower)alkyl; and $R^4$ is hydrogen, or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to produce analgesia in a mammal in need thereof by administering to the mammal an effective analgesic amount of a compound of formula I or a therapeutically acceptable acid addition salt thereof.

The compounds of formula I or a therapeutically acceptable acid addition salt thereof can be prepared by selecting a process from the group of:

(a) cyclodehydrating a hydrazide of formula II

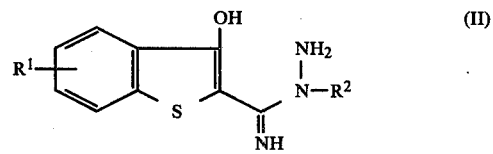

in which $R^1$ and $R^2$ are as defined herein to obtain the corresponding compound of formula I in which $R^1$ and $R^2$ are as defined herein, and $R^3$ and $R^4$ are hydrogen;

(b) subjecting the compound of formula I in which $R^1$ and $R^2$ are as defined herein, and $R^3$ and $R^4$ are hydrogen to acylation, reduction or alkylation, in optional order and to the extent required to obtain the corresponding compound of formula I, in which $R^1$ and $R^2$ are as defined herein; $R^3$ is lower alkyl; trihalomethyl(lower)alkyl; oxo(lower)alkyl; or lower alkanoyl; and $R^4$ is hydrogen or lower alkyl; and (c) reacting a compound of formula I, in which $R^1$, $R^2$, $R^3$ and $R^4$ are as defined herein with a therapeutically acceptable acid to obtain the corresponding compound and formula I, as the salt with a therapeutically acceptable acid.

DETAILED DESCRIPTION OF THE INVENTION

The term "lower alkyl" as used herein means straight and branched chain alkyl radicals containing from one to six carbon atoms, preferably one to three carbon atoms, and includes methyl, ethyl, propyl, 1-methylethyl, butyl, 1,1-dimethylethyl and pentyl, unless stated otherwise.

The term "halo" as used herein means halo radicals and includes fluoro, chloro, bromo and iodo, unless stated otherwise.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "lower alkanoyl" as used herein means straight chain 1-oxoalkyl radicals containing from two to six carbon atoms and branched chain 1-oxoalkyl radicals containing four to six carbon atoms and includes acetyl, 1-oxopropyl, 2-methyl-1-oxopropyl, 1-oxohexyl and the like.

The term "oxo(lower)alkyl" as used herein means straight chain oxoalkyl radicals containing from two to six carbon atoms and branched chain oxoalkyl radicals containing four to six carbon atoms wherein the oxo function is located at a carbon atom other than position 1 of the lower alkyl chain, and includes 2-oxoethyl, 3-oxobutyl, 2-ethyl-3-oxobutyl and the like.

The term "lower alkanol" as used herein means both straight and branched chain alkanols containing from one to four carbon atoms and includes methanol, ethanol, isopropanol, butanol and the like.

The term "lower alkanoic acid" as used herein means both straight and branched chain alkanoic acids containing from one to six carbon atoms and includes formic acid, acetic acid, propanoic acid, 3-methylbutanoic acid and the like.

The term "organic proton acceptor" as used herein means the organic bases or amines, for instance, triethylamine, pyridine, N-ethylmorpholine and 1,5-diazabicyclo[4.3.0]non-5-ene.

The term "inorganic proton acceptor" as used herein means the inorganic bases, preferably the alkali methyl hydroxides, carbonates and bicarbonates, for example, sodium hydroxide, potassium hydroxide, sodium carbonate, sodium bicarbonate and potassium carbonate.

The term "proton acceptor" as used herein means a proton acceptor selected from an organic proton acceptor and inorganic proton acceptor, as defined hereinabove.

The term "complex metal hydride" as used herein means metal hydride reducing agents and includes, for example, lithium aluminum hydride, lithium aluminum hydride-aluminum chloride, aluminum hydride-aluminum chloride, diborane, diisobutylaluminum hydride, borane methyl sulfide and sodium borohydride-aluminum chloride.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic additives as the corresponding bases. For many purposes it is preferable to administer the salts rather than the base compounds. Examples of suitable acids to form these salts include: the common mineral acids, e.g., hydrohalic, sulfuric or phosphoric acids, the organic acids, e.g., formic, acetic, maleic, methanesulfonic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in their therapeutic use. Hence, these addition salts are included within the scope of this invention and are limited only by the requirement that the acids employed in forming the salts be therapeutically acceptable.

The novel compounds of formula I exhibit useful biological activities in several pharmacological tests. The compounds of formula I exert valuable analgesic effects in a mammal. Futhermore, some of the compounds of formula I are useful for inhibiting convulsions, anxiety and aggression, for producing muscle relaxation, and hypnosis, and for inhibiting gastric acid secretion in a mammal.

The analgesic activity of the compounds of formula I or their acid addition salts with therapeutically acceptable acids can be demonstrated in standard pharmacologic tests such as, for example, the test described by S. Ankier, European Journal of Phamacology, 27, 1 (1974). In this test for analgesia, the hot plate apparatus (Analgesia Meter Model 475, Technilab Instruments, Inc., Pequannock, N.J., U.S.A.) was heated to a temperature of 55° C. Male albino mice weighing 18–23 g were used. The control vehicle and compound were each administered intraperitoneally to separate groups of 10 mice which were then tested at durations of 20 min and 40 min from the time of injection. For each control testing, the average reaction time (amount of time elapsed until the mouse shook or licked a hindpaw) was calculated and multiplied by 1.5. This figure was designated as the "analgesic value" or A.V. A maximum cut-off time of 60 sec. was used to avoid tissue damage. A mouse whose reaction time equalled, or exceeded this value was considered analgesic. From these values an $ED_{50}$ was calculated.

Using the above method, the compounds of formula I exhibit analgesic effects in mice at an i.p. dose in the range from about 10 to 250 mg per kg of body weight. For example, the following representative compound is an effective analgesic agent when administered intraperitoneally to the mouse (the effective i.p. dose to obtain the $ED_{50}$ in mg per kg of body weight is given in the parentheses): 2-methyl-2H-benzothieno[3,2-c]pyrazol-3-amine (66 mg/kg).

In addition, the anticonvulsant activity of most of the compounds of formula I or a therapeutically acceptable acid addition salt thereof can be shown by using the test described by E. A. Swinyard et al., J. Pharmacol. Exp. Ther., 106, 319 (1952) for the inhibition of maximal electroshock. In this test for anticonvulsant activity, electroconvulsions were produced using corneal electrodes and alternating current of supramaximal intensity (30 mA, 0.2 sec.). Groups of 10 mice were injected with the test compound i.p., or the vehicle 60 min before being subjected to electroshock. The results are expressed as the percent of mice protected from the hind limb tonic extensor component.

Using the latter method, the compounds of formula I exhibit anticonvulsant activity in mice at an i.p. dose in the range from about 30 to about 500 mg per kg of body weight. For example, the following representative compound is an effective anticonvulsant agent when administered intraperitoneally to the mouse (the effective i.p. dose to obtain the $ED_{50}$ in mg per kg of body weight is given in the parentheses): 2-methyl-2H-benzothieno[3,2-c]pyrazol-3-amine (120 mg/kg).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as analgesic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective analgesic amount of the compounds for i.p. administration usually ranges from about 10 mg to about 250 mg per kilogram body weight per day in single or divided doses although as aforementioned variations will occur. However a dosage level that is in the range of from about 25 to about 150 mg per kilogram body weight per day in single or divided doses is employed most desirably for i.p. administration in order to achieve effective results. For oral administration, effective amounts can range from about 25 to 500 mg per kilogram body weight per day in single or divided doses preferably about 40 to 400 mg per kilogram of body weight per day.

A compound of formula I or a therapeutically acceptable acid addition salt thereof can also be used to produce beneficial analgesic effects when combined with a therapeutically effective amount of an agent commonly used for analgesia. The combination produces an analgesic effect which is either additive of the individual agents or greater than each individual agent alone. Such commonly used analgesic agents include, for example, acetylsalicyclic acid, acetaminophen, aminopyrine, codeine, morphine, and the like. Suitable methods of administration, compositions and dosages of the agents are well known in the art, for instance, "Physicians' Desk Reference", 36th ed., Medical Economics Co., Oradell, N.J., U.S.A., 1982 and "AMA Drug Evaluations", 3rd ed., PSG Publishing Company, Inc., Littleton, Mass., U.S.A., 1977. When used in combination, a compound of formula I or its therapeutically acceptable acid addition salt is administered as previously described; however, a lower dose can be used for efficacious results.

The compounds of formula I are prepared in the following manner.

The following reaction illustrates a method for preparing the intermediate of formula II

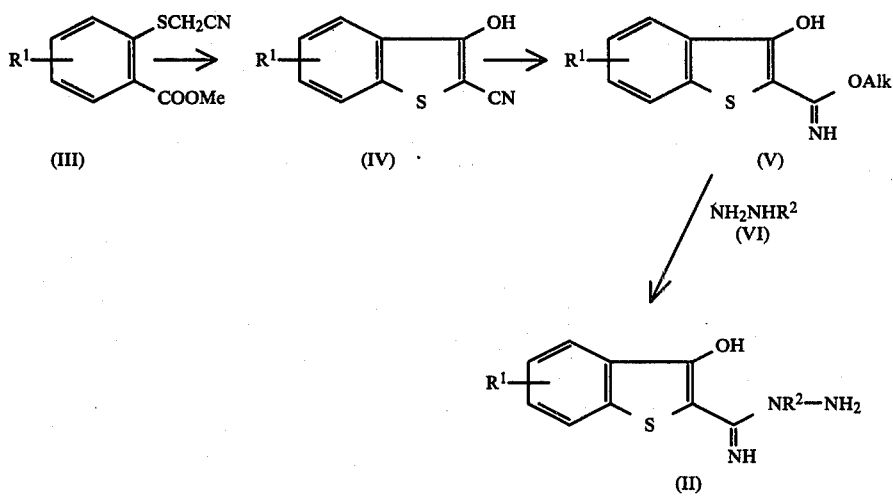

Many of the acetonitriles of formula III are described in the chemical literature, e.g. K. Görlitzer, Arch. Pharmaz., 308, 700 (1975), or can be prepared by known methods, e.g. by those described by Görlitzer.

Cyclization of the acetonitrile of formula III with sodium methoxide in an inert solvent, affords the corresponding carbonitrile of formula IV in which $R^1$ is as defined herein. Some of the carbonitriles of formula IV are known, for example, K. Görlitzer, cited above.

The carbonitrile of formula IV is readily converted into the corresponding carboximidate of formula V in which $R^1$ is as defined herein and Alk is lower alkyl having one to four carbon atoms by reacting the carbonitrile with a lower alkanol in the presence of dry hydrogen chloride at 0° to 50° C. for 0.5 to 10 hours and isolating the carboximidate of formula V as the hydrochloride salt.

Reaction of the carboximidate of formula V with about one to five molar equivalents of a hydrazine of formula VI in which $R^2$ is as defined herein in an inert solvent gives the corresponding hydrazide of formula II in which $R^1$ and $R^2$ are as defined herein. A preferred solvent for the reaction in benzene or acetonitrile and the reaction is conducted preferably at about 20° to 100° C. for about one hour to three days.

Cyclodehydration of the hydrazide of formula II with a dehydrating agent gives the corresponding compound of formula I in which $R^1$ and $R^2$ are as defined herein, and $R^3$ and $R^4$ are hydrogen. An excess of a dehydrating agent is used for this cyclization, for example, polyphosphoric acid, trifluoroacetic acid and phosphorus oxychloride. Polyphosphoric acid is the preferred dehydrating agent. Usually, the cyclodehydration is conducted at about 50° to 125° C. for about two to 15 hours.

If desired, the compounds of formula I, prepared as described above, can be converted to other compounds of formula I.

In one conversion, the compound of formula I in which $R^1$ and $R^2$ are as defined herein, and $R^3$ and $R^4$ are lower hydrogen are acylated to obtain the corresponding compound of formula I in which $R^1$ and $R^2$ are as defined herein, $R^3$ is lower alkanoyl, and $R^4$ is hydrogen. Any of the usual methods of acylation can be used. For example, reaction with about one to five molar equivalents of a lower alkanoyl chloride or bromide in the presence of a proton acceptor in an inert organic solvent at about 0° to 50° C. for one to ten hours affords the corresponding compound of formula I in which $R^3$ is lower alkanoyl and $R^4$ is hydrogen. In another acylation method, reaction of the compound of formula I in which $R^1$ and $R^2$ are as defined herein, and $R^3$ and $R^4$ are hydrogen with about one to ten molar equivalents of an anhydride of a lower alkanoic acid at 0° to 50° C. for one to ten hours gives the corresponding compound of formula I in which $R^3$ is lower alkanoyl and $R^4$ is hydrogen. In the latter method, the anhydride can act as the solvent or an inert organic solvent can be used.

Reduction of the latter compound of formula I in which $R^3$ is lower alkanoyl gives the corresponding compound of formula in which $R^1$ and $R^2$ are as defined herein, $R^3$ is a lower alkyl having a methylene group adjacent the nitrogen, and $R^4$ is hydrogen. The reduction is best performed with an excess of a complex metal hydride. A preferred method of reduction uses about three to ten molar equivalents of diborane, as reducing agent, in an inert organic solvent, preferably tetrahydrofuran, at 50° to 100° C. for about one to ten hours.

Another conversion involves the alkylation of the compound of formula I in which $R^1$ and $R^2$ are as defined herein, and $R^3$ and $R^4$ are hydrogen with about one molar equivalent of a lower alkyl bromide, chloride or iodide in the presence of an inorganic or organic proton acceptor in an inert organic solvent to give the corresponding compound of formula I in which $R^1$ and $R^2$ are as defined herein, $R^3$ is lower alkyl and $R^4$ is hydrogen. This alkylation is performed usually at 5° to 50° C. for one to ten hours.

The compounds of formula I in which $R^1$ and $R^2$ are as defined herein, $R^3$ is oxo(lower)alkyl and $R^4$ is hydrogen can be prepared by alkylating the corresponding compound of formula I in which $R^1$ and $R^2$ are as defined herein, and $R^3$ and $R^4$ are hydrogen with about one molar equivalent of an oxo(lower)alkyl bromide, chloride or iodide in the same manner as described in the latter alkylation. Other methods are also available for preparing some of the compounds of formula I in which $R^3$ is oxo(lower)alkyl. For example, a preferred method of preparing the compounds of formula I in which $R^1$ and $R^2$ are as defined herein, $R^3$ is 3-oxobutyl and $R^4$ is hydrogen involves the reaction of the corresponding compound of formula I in which $R^3$ and $R^4$ are hydrogen with methyl vinyl ketone; generally, one to five molar equivalents of methyl vinyl ketone is employed in an inert organic solvent at about 10° to 40° C. for about 10 to 30 hours.

Compounds of formula I in which $R^1$ and $R^2$ are as defined herein, $R^3$ is trihalomethyl(lower)alkyl, and $R^4$ is hydrogen can be prepared by alkylating the corresponding compound of formula I in which $R^1$ and $R^2$ are as defined herein, and $R^3$ and $R^4$ are hydrogen with about one molar equivalent of a trihalomethyl(lower)alkyl bromide, chloride or iodide in the same manner as described in the latter alkylation. Some compounds of formula I in which $R^3$ is trihalomethyl(lower)alkyl can be prepared by other methods. For instance, acylation of the compound of formula I in which $R^3$ and $R^4$ are hydrogen with a trihalomethyl(lower)alkylcarbonyl chloride or bromide, or an anhydride of a trihalomethyl(lower)alkylcarboxylic acid, in the same manner as described above for the preparation of the compounds of formula I in which $R^3$ is lower alkanoyl and reduction of the resulting amide with a complex metal hydride affords the corresponding compound of formula I in which $R^1$ and $R^2$ are as defined herein, $R^3$ is trihalomethyl(lower)alkyl having a methylene group adjacent the nitrogen, and $R^4$ is hydrogen. Preferably, the reduction is conducted with an excess of lithium aluminum hydride, as reducing agent, in an inert organic solvent, i.e. tetrahydrofuran, at about 30° to 80° C. for about 15 minutes to five hours.

The following example illustrates further this invention.

EXAMPLE 1

A solution of methyl thiosalicylate (164 g, 0.975 mol) in methanol (1.1 L) was added in one portion to a cold solution of freshly prepared sodium methoxide (from 25.5 g, 1.1 mol Na-metal in methanol, 1.1 L). The salt solution was cooled to 0° C. and a cold (0° C.) solution of chloroacetonitrile (83.7 g, 1.1 mol) in methanol (0.5 L) was added in one portion with stirring. After several minutes a strong precipitate appeared. After standing for several days at room temperature, the precipitate was collected, washed with ice-cold methanol, then washed well with water and dried to give 141.0 g of 2-(2-carbomethoxyphenylthio)acetonitrile, mp 120°–122° C. [described by K. Görlitzer, Arch. Pharmaz., 308, 700 (1975)].

To a warm solution (40°–50° C.) of the latter compound (41.15 g, 0.2 mol) in dry benzene (018 L), powdered sodium methoxide (16.2 g, 0.3 mol) was added in one portion with stirring. After 2 hr of refluxing, additional sodium methoxide (0.1 mol) was added and the solution was refluxed for 1.5 hr. After cooling, water (0.5 L) was added, and the aqueous phase was separated and filtered (through soft filter paper) to remove small impurities. Then slowly, the filtrate was added with stirring to dilute hydrochloric acid. The precipitate was collected, washed with water, and dissolved in hot chloroform (ca 1 L). The solution was dried (MgSO$_4$), filtered hot, concentrated. The crystals were collected in two crops of 25.2 and 1.3 g, both of mp ca 175° C. (dec.), to give 3-hydroxybenzo[b]-thiophene-2-carbonitrile (K. Görlitzer, cited above, found mp 163° C. (dec.) for this compound).

To a solution of the latter compound (20.0 g, 0.114 mol) in ethanol (200 mL), dry hydrogen chloride (105 g) was introduced keeping the reaction temperature at 20°–25° C. with ice-water cooling. After stirring for 2.5 days at room temperature the yellow precipitate was collected and dried at room temperature in vacuo to give 23.84 g of pink crystals of ethyl (3-hydroxybenzo[b]thiophene)-2-carboximidate hydrochloride: mp 205°–207° C. (dec.); IR (mineral oil) 3360, 3300, 2400 and 1660 cm$^{-1}$; NMR (DMSO-d$_6$) δ 1.4 (3H, t), 4.55 (2H, q), 7.7 (4H, m) and 9.35 (2H, broad); and Anal. Calcd for C$_{11}$H$_{11}$NO$_2$S.HCl: C, 51.26% H, 4.69% N, 5.43% and Found: C, 51.26% H, 4.69% N, 5.42%.

The latter compound (7.4 g, 28.7 mmol) was suspended in acetonitrile (150 mL) and methyl hydrazine (6 mL, ca 3 mol. equiv. excess) was added in one portion. After stirring for 2.5 days at room temperature, the precipitate was collected, washed with acetonitrile and diethyl ether, and dried to give 8.21 g of a yellow product, mp 195° C. (dec.). A sample was recrystallized from methanol to give 3-hydroxybenzo[b]thiophene-2-carboximidic acid, 1-methylhydrazide: mp 235°–236° C. (dec); IR (mineral oil) 3200 and 3300 cm$^{-1}$; NMR (DMSO-d$_6$) δ 3.2 (3H, s) and 7.5 (4H, m); and Anal. Calcd for C$_{10}$H$_{11}$N$_3$OS: C, 54.28% H, 5.01%, N, 18.99% and Found: C, 53.92% H, 4.94% N, 18.94%.

The latter compound (8.0 g) was combined with polyphosphoric acid (100 g). The mixture was heated and stirred at ca 50° C. until foaming from hydrogen chloride-evolution subsided (ca 1 hr), and then heated at 95°–100° C. (bath temp) for 3 hr. With external cooling, crushed ice and water was added to ca double volume. With cooling, 50% aqueous sodium hydroxide was slowly added. Additional water was added to dissolve precipitating inorganic phosphate salts. The mixture was adjusted to pH 9 and the precipitate was extracted into chloroform (not well soluble). The organic solution was washed with water, dried and taken to dryness to give 5.1 g of beige crystals, mp ca 225°–230° C. The product (5.0 g) was recrystallized from isopropanol (charcoal) to give 3.92 g of 2-methyl-2H-benzothieno[3,2-c]pyrazol-3-amine: mp 233° C.; IR (mineral oil) 3410, 3260, 3080 and 1635 cm$^{-1}$; UV max (MeOH) 323 nm (ε=3820), 256 (23295) and shoulder 226; NMR (DMSO-d$_6$) δ 3.75 (3H, s), 5.7 (1H, s) and 7.5 (4H, m); Anal. Calcd for C$_{10}$H$_9$N$_3$S: C, 59.09% H, 4.46% N, 20.67% and Found: C, 58.95% H, 4.44% N, 20.63%.

The latter compound was converted to the corresponding hydrochloride salt and crystallized from methanol-diethyl ether: mp 247°–250° C. (dec) and Anal. Calcd for C$_{10}$H$_9$N$_3$S.HCl: C, 50.10% H, 4.20% N, 17.53% and Found: C, 50.05% H, 4.22% N, 17.80%.

Similarly preparable are:

N,6-diethyl-N-methyl-2-propyl-2H-benzothieno[3,2-c]pyrazol-3-amine, 7-bromo-2-ethyl-N-methyl-N-trifluoromethyl-2H-benzothieno[3,2-c]pyrazol-3-amine, 2-butyl-N-(3-oxobutyl)-5-propoxy-2H-benzothieno[3,2-c]pyrazol-3-amine, N-acetyl-2-(1-methylethyl)-N-propyl-8-trifluoromethyl-2H-benzothieno[3,2-c]-pyrazol-3-amine, N-butyl-2,6-dipentyl-2H-benzothieno[3,2-c]pyrazol-3-amine, 2,7-dimethyl-2H-benzothieno[3,2-c]pyrazol-3-amine, or 6-chloro-2-methyl-2H-benzothieno[3,2-c]pyrazol-3-amine.

We claim:

1. An analgesic composition, which comprises an effective amount of a compound of the formula

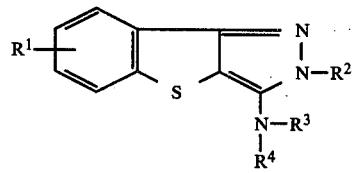

in which R$^1$ is hydrogen, halogen, lower alkyl, lower alkoxy or trifluoromethyl; R$^2$ is lower alkyl; R$^3$ is hydrogen, lower alkyl, trihalomethyl(lower)alkyl; oxo(lower)alkyl; or lower alkanoyl; and R$^4$ is hydrogen or lower alkyl; or a therapeutically acceptable acid addition salt thereof, and a pharmaceutically acceptable carrier therefor.

2. The composition of claim 1 wherein in the compound therein R$^1$ is hydrogen, bromo, chloro or lower alkyl; R$^2$ is methyl; R$^3$ is hydrogen, lower alkyl, trifluoromethyl(lower)alkyl or oxo(lower)alkyl; and R$^4$ is hydrogen, or a therapeutically acceptable acid addition salt thereof.

3. The composition of claim 2 where the compound therein is 2-methyl-2H-benzothieno[3,2-c]pyrazol-3-amine.

4. The composition of claim 3 wherein the compound therein is the hydrochloride salt thereof.

5. A method of producing analgesia in a mammal, which comprises administering to the mammal an effective analgesic amount of a composition of claim 1 or a therapeutically acceptable acid addition salt thereof.

* * * * *